(12) United States Patent
Suon

(10) Patent No.: US 6,331,183 B1
(45) Date of Patent: Dec. 18, 2001

(54) BASKET FILTER

(75) Inventor: Naroun Suon, Lawrence, MA (US)

(73) Assignee: SciMed Life Systems, Inc., Maple Grove, MN (US)

( * ) Notice: Subject to any disclaimer, the term of this patent is extended or adjusted under 35 U.S.C. 154(b) by 0 days.

(21) Appl. No.: 09/404,530

(22) Filed: Sep. 23, 1999

Related U.S. Application Data

(60) Provisional application No. 60/101,611, filed on Sep. 24, 1998.

(51) Int. Cl.$^7$ .................................................. A61M 29/00
(52) U.S. Cl. ............................................................ 606/200
(58) Field of Search ..................................... 606/700, 191, 606/194

(56) References Cited

U.S. PATENT DOCUMENTS

| | | |
|---|---|---|
| 4,425,908 | 1/1984 | Simon . |
| 4,643,184 | 2/1987 | Mobin-Uddin . |
| 4,832,055 * | 5/1989 | Palestrant ........................ 128/899 |
| 5,234,458 | 8/1993 | Metais . |
| 5,300,086 | 4/1994 | Gory et al. . |
| 5,329,942 | 7/1994 | Gunther et al. . |
| 5,601,595 | 2/1997 | Smith . |
| 5,634,942 | 6/1997 | Chevillon et al. . |
| 5,810,874 | 9/1998 | Lefebvre . |

* cited by examiner

Primary Examiner—Gene Mancene
Assistant Examiner—Eduardo C. Robert
(74) Attorney, Agent, or Firm—Crompton, Seager & Tufte LLC

(57) ABSTRACT

A thrombus filter element for placement within a blood vessel lumen defined by a blood vessel wall is disclosed. A thrombus filter element in accordance with the present invention includes a hub having a proximal end, a distal end, and a lumen extending therethrough, a plurality of wires extending from the hub, at least one end of each wire being fixed to the hub proximate the proximal end thereof, a plurality of struts radiating away from the hub, the fixed end of each strut being fixed to the hub proximate the distal end thereof, and a slider rod slidingly disposed within the lumen of the hub.

22 Claims, 2 Drawing Sheets

BASKET FILTER

CROSS REFERENCE TO RELATED APPLICATION

The present application claims the benefit of U.S. Provisional Application Ser. No. 60/101,611, filed Sep. 24, 1998.

FIELD OF THE INVENTION

The present invention pertains to the field of intra vena cava filters. In particular, the present invention pertains to the retrieval of intra vena cava filters.

Intra vena cava filters are commonly implanted either temporarily or permanently in patients at risk for blood clotting.

BACKGROUND OF THE INVENTION

There are a number of situations in the practice of medicine when it becomes desirable for a physician to place a filter in the vascular system of a patient. One of the most common applications for vascular filters is the treatment of Deep Venous Thrombosis (DVT). Deep Venous Thrombosis patients experience clotting of blood in the large veins of the lower portions of the body. These patients are constantly at risk of a clot breaking free and traveling via the inferior vena cava to the heart and lungs. This process is known as pulmonary embolization. Pulmonary embolization can frequently be fatal, for example when a large blood clot interferes with the life-sustaining pumping action of the heart. If a blood clot passes through the heart it will be pumped into the lungs and may cause a blockage in the pulmonary arteries. A blockage of this type in the lungs will interfere with the oxygenation of the blood causing shock or death.

Pulmonary embolization may be successfully prevented by the appropriate placement of a thrombus filter in the vascular system of a patient's body. Placement of the filter may be accomplished by performing a laparotomy with the patient under general anesthesia. However, intravenous insertion is often the preferred method of placing a thrombus filter in a patient's vascular system.

Intravenous insertion of a thrombus filter is less invasive and it requires only a local anesthetic. In this procedure, the thrombus filter is collapsed within a delivery catheter. The delivery catheter is introduced into the patients vascular system at a point which is convenient to the physician. The delivery catheter is then fed further into the vascular system until it reaches a desirable location for filter placement. The thrombus filter is then released into the blood vessel from the delivery catheter.

In the treatment of Deep Venous Thrombosis, a thrombus filter is placed in the inferior vena cava of a patient. The inferior vena cava is a large vessel which returns blood to the heart from the lower part of the body. The inferior vena cava may be accessed through the patient's femoral vein.

Thrombus filters may be placed in other locations when treating other conditions. For example, if blood clots are expected to approach the heart and lungs from the upper portion of the body, a thrombus filter may be positioned in the superior vena cava. The superior vena cava is a large vessel which returns blood to the heart from the upper part of the body. The superior vena cava may by accessed through the jugular vein, located in the patient's neck.

Once placed inside a blood vessel, a thrombus filter acts to catch and hold blood clots. The flow of blood around the captured clots allows the body's lysing process to dissolve the clots.

SUMMARY OF THE INVENTION

The present invention pertains to an intra vena cava filter implantable temporarily or permanently, and methods for removal thereof. The filter is held in place in a vein or other organ by friction fit between the basket portion and the wall of the vein or other organ. Additionally, the struts have sharpened tips which engage the wall of the vein or inner surface of another organ to enhance positional stability of the filter.

DETAILED DESCRIPTION OF THE INVENTION

The following detailed description should be read with reference to the drawings, in which like elements in different drawings are numbered identically. The drawings which are not necessarily to scale, depict selected embodiments and are not intended to limit the scope of the invention. Examples of constructions, materials, dimensions, and manufacturing processes are provided for selected elements. Those skilled in the art will recognize that many of the examples provided have suitable alternatives which may be utilized.

Figure 1:
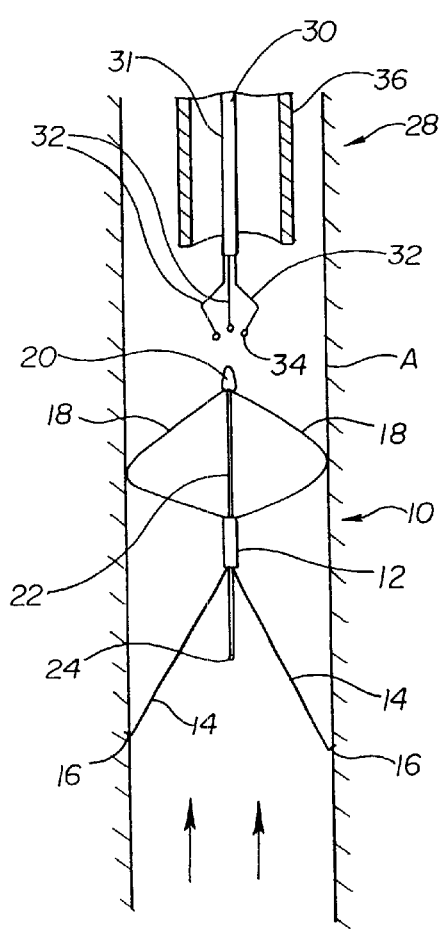
FIG. 1 is a view of the filter in accordance with the present invention disposed within a vessel, and a removal device.

Referring now to the drawings wherein like reference numerals refer to like elements throughout the several views, FIG. 1 is a side view of a preferred embodiment of a filter 10 in accordance with the present invention disposed within vessel or vena cava A. Filter 10 includes a generally tubular hub 12 from which extends a plurality of struts 14. Two struts 14 are shown in FIG. 1, however, preferably six struts are evenly spaced in a generally conical formation. Additionally, each strut 14 can include bends along their length to catch thrombus which flows through vessel A in the direction of the arrows. The struts of the present invention are preferably arranged in a manner similar to the Greenfield™ filter made by Medi-Tech (Watertown, Mass.). The end of each strut preferably includes a sharpened tip 16 for engagement with the vessel wall to stabilize filter 10 within vessel A.

Extending from hub 12 opposite struts 14 are preferably, preformed, flattened wires 18. An end of each wire 18 opposite hub 12 is preferably coupled to a coupling 20. As shown in FIG. 1, two wires 18 are disposed between hub 12 and coupling 20. There are, however, preferably four equally spaced wires 18 forming a basket portion of the filter. The basket portion of the filter may be generally bulbous in shape. The basket portion of the filter may also be ball shaped. In the embodiment of FIG. 1, the shape of the basket portion of the filter may be described as an elliptical rotation. A slider rod 22, having a stop, or ball tip 24, is connected to coupling 20 and disposed through hub 12. Slider rod 22 is preferably, fixably connected to coupling 22, and slidable longitudinally within hub 12.

In a presently preferred embodiment, wires 18 are made from a shape memory alloy such as NiTi alloy. In a presently most preferred embodiment, wires 18 are preferably preset to expand radially to meet the walls of vessel A at approximately 37° C. (body temperature) when placed in vessel A. It is anticipated that wires 18 may be comprised of other biocompatible materials.

Embodiments of the present invention have also been envisioned, in which wires 18 are mechanically biased to expand radially toward the walls of vessel A if unconstrained. Wires 18 may be comprised of metallic or non-metallic materials. Examples of metallic materials which may be suitable in some applications include stainless steel. Examples of non-metallic materials which may be suitable in some applications are included in the list below which is not exhaustive: polycarbonate, poly(L-lactide) (PLLA), poly(D,L-lactide) (PLA), polyglycolide (PGA), poly(L-lactide-co-D,L-lactide) (PLLA/PLA), poly(L-lactide-co-glycolide) (PLLA/PGA), poly(D, L-lactide-co-glycolide) (PLA/PGA), poly(glycolide-co-trimethylene carbonate) (PGA/PTMC), polyethylene oxide (PEO), polydioxanone (PDS), polycaprolactone (PCL), polyhydroxylbutyrate (PHBT), poly (phosphazene), polyD,L-lactide-co-caprolactone) (PLA/PCL), poly(glycolide-co-caprolactone) (PGA/PCL), polyanhydrides (PAN), poly(ortho esters), poly(phoshate ester), poly(amino acid), poly(hydroxy butyrate), polyacrylate, polyacrylamid, poly(hydroxyethyl methacrylate), polyurethane, polysiloxane and their copolymers.

A removal device 28 is disposed above filter 10 in FIG. 1. Device 28 includes a stabilizer 30 and a catheter 36. Catheter 36 could be made in a manner similar to a guide catheter. Stabilizing device 30 preferably includes a tubular shaft 31 having a proximal end (not shown) and a distal end. Preferably extending between the proximal end and the distal end are elongate members 32 having a distal end extending beyond the distal end of shaft 31. The distal end of members 32 are preferably bent to form a claw as shown. Atraumatic balls 34 can be disposed at the distal end of members 32. Removal device 28 can be placed in the position shown by way of a jugular vein access point.

Figure 2:
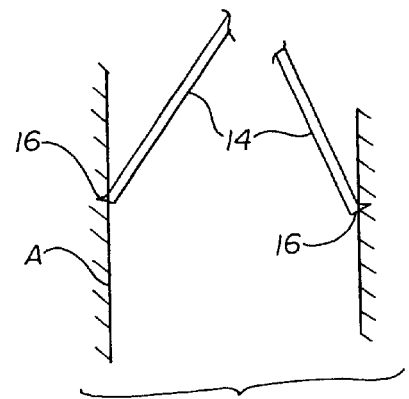
FIG. 2 is a detailed view of sharpened ends of struts of the filter of FIG. 1.

FIG. 2 is a detailed view of the sharpened tips 16 of struts 14 of FIG. 1. Sharpened tips 16 are preferably bent relative to the longitudinal axis of struts 14 such that tips 16 engage the wall of vena cava A approximately perpendicularly.

Figure 3:
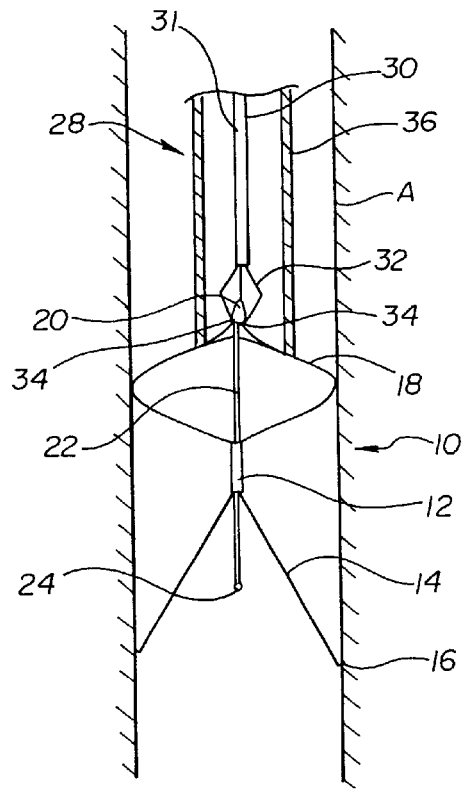
FIG. 3 is a view of the filter of FIG. 1, wherein the removal device is attached to the filter.

FIG. 3 is a view of filter 10 of FIG. 1 in which the claw portion of stabilizing device 30 has been brought into contact with coupling 20. Atraumatic balls 34 as shown engaging a portion of coupling 20 to hold filter 10. The claw portion of device 30 can be closed to grasp coupling 20 by advancing shaft 31 over members 32 to engage the claw portion forcing balls 34 toward each other. Once filter 10 is grasped by stabilizer 30, catheter 36 can be advanced into engagement with wires 18.

Figure 4:
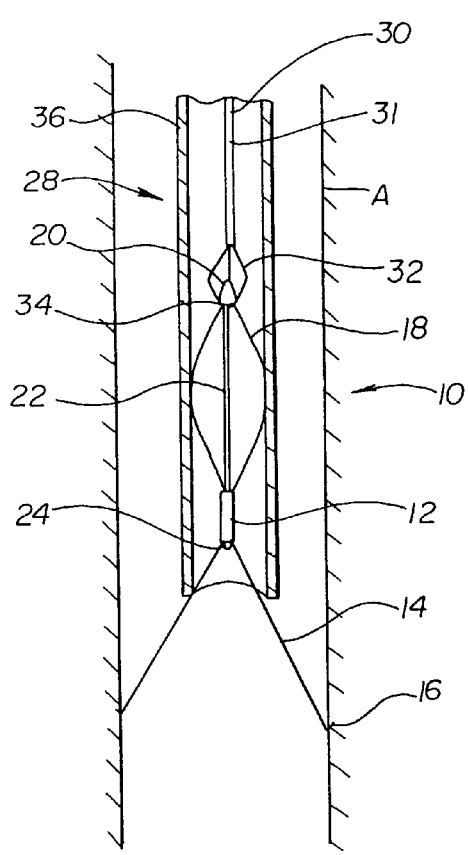
FIG. 4 is a view of the filter of FIG. 1, wherein the filter is partially within into the removal device.
Figure 5:
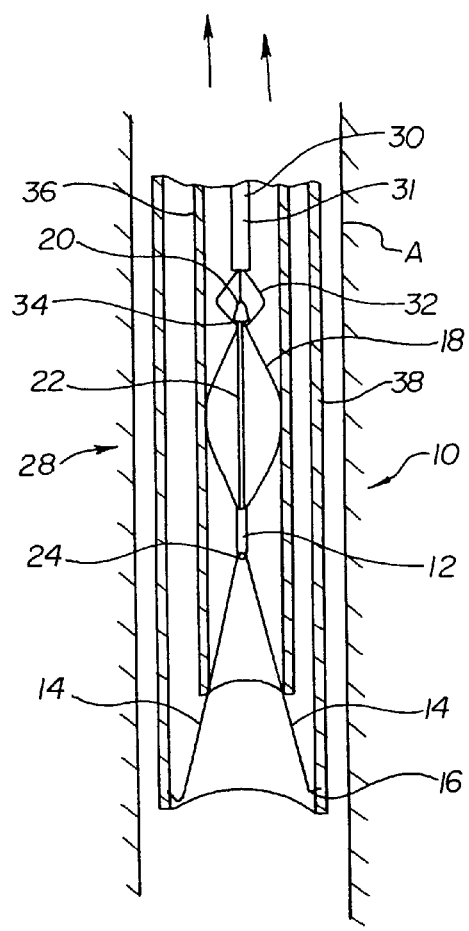
FIG. 5 is a view of the filter of FIG. 1, wherein a sheath is disposed over the filter.

FIG. 4 shows the filter of FIG. 1, wherein catheter 36 has been advanced further than as shown in FIG. 3, to engage struts 14. In FIG. 5, catheter 36 has been advanced yet further to compress struts 14 inwardly to draw sharpened tips 16 away from the wall of vessel A. A second catheter 38 has been advanced over the entire filter 10 to shield the vessel wall from tips 16 during subsequent removal of filter 10 in the direction shown by the arrows. It can be appreciated by those skilled in the art, that a method substantially similar to that shown and described herein with respect to the preceding figures can be preformed in reverse to place filter 10 within vena cava A.

Numerous characteristics and advantages of the invention covered by this document have been set forth in the foregoing description. It will be understood, however, that this disclosure is, in many respects, only illustrative. Changes may be made in details, particularly in matters of shape, size and ordering of steps without exceeding the scope of the invention. The invention's scope is, of course, defined in the language in which the appended claims are expressed.

What is claimed is:

1. A thrombus filter element for placement within a blood vessel lumen defined by a blood vessel wall, comprising:
   a hub having a proximal end, a distal end, and a lumen extending therethrough;
   a plurality of wire extending proximally from the hub;
   each wire having a first end and a second end;
   the first end of each wire being fixed to the hub proximate the proximal end thereof;
   the second end of each wire being fixed to a coupling;
   the plurality of wires being mechanically biased to expand radially toward the blood vessel walls and to form a basket;
   a plurality of struts radiating distally away from the hub;
   each strut having a free end and a fixed end;
   the fixed end of each strut being fixed to the hub proximate the distal end thereof;
   the plurality struts being arranged to form an array;
   a slider rod slidingly disposed within the lumen of the hub;
   the slider rod having a distal end and a proximal end; and
   the proximal end of the slier rod being fixed to the coupling.

2. The thrombus filter of claim 1, wherein the plurality of struts are disposed in a generally conical formation.

3. The thrombus filter of claim 1, further including an anchoring element disposed proximate a proximal end of each strut.

4. The thrombus filter of claim 1, further including an anchoring element disposed proximate a proximal end of each strut;
   each anchoring element including a sharpened tip.

5. The thrombus filter of claim 1, further including a stop disposed at the distal end of the slider rod.

6. The thrombus filter of claim 1, wherein each strut includes a plurality of bends.

7. The thrombus filter of claim 1, wherein the basket is generally bulbous in shape.

8. The thrombus filter of claim 1, wherein the wires are comprised of shape memory material.

9. The thrombus filter of claim 1, wherein the wires are comprised of Nitinol.

10. The thrombus filter of claim 1, wherein the struts are biased to expand radially.

11. The thrombus filter of claim 1, wherein the basket is biased to expand radially.

12. The thrombus filter of claim 1, wherein the wires are biased to expand radially.

13. The thrombosis filter of claim 1, wherein the wires are comprised of shape memory material, and the wires are preset to expand radially when the temperature of the shape-memory material is generally body temperature.

14. A thrombus filter element for placement within a blood vessel lumen defined by a blood vessel wall, comprising:
   a hub having a proximal end, a distal end, and a lumen extending therethrough;
   a plurality of wires extending proximally from the hub;

each wire having a first end and a second end;

the first end of each wire being fixed to the hub proximate the proximal end thereof;

the second end of each wire being fixed to a coupling;

the plurality of wires being mechanically biased to expand radially toward the blood vessel walls and to form a basket;

a plurality of struts radiating distally away from the hub;

each strut having a free end and a fixed end;

the fixed end of each strut being fixed to the hub proximate the distal end thereof;

an anchoring element fixed to each strut proximate the free end thereof;

wherein each anchoring element is adapted to engage the blood vessel wall;

the plurality struts being arranged to form an array;

the array being generally conical in shape;

a slider rod having a distal end and a proximal end;

the proximal end of the slider rod being fixed to the coupling; and a stop disposed about the slider rod proximate the distal end thereof.

15. The thrombus filter of claim 14, wherein each anchoring element includes a sharpened tip.

16. The thrombus filter of claim 14, wherein each strut includes a plurality of bends.

17. The thrombus filter of claim 14, wherein the wires are comprised of shape memory material.

18. The thrombus filter of claim 14, wherein the wires are comprised of Nitinol.

19. The thrombus filter of claim 14, wherein the struts are biased to expand radially.

20. The thrombus filter of claim 14, wherein the basket is biased to expand radially.

21. The thrombus filter of claim 14, wherein the wires are biased to expand radially.

22. The thrombosis filter of claim 14, wherein the wires are comprised of shape memory material, and the wires are preset to expand radially when the temperature of the shape-memory material is generally bodily temperature.

* * * * *